US010500438B1

(12) United States Patent
Lemire (10) Patent No.: US 10,500,438 B1
(45) Date of Patent: Dec. 10, 2019

(54) BODY POSTURAL ANALYSIS AND CORRECTIVE EXERCISE MAT AND METHOD OF UTILIZATION

(71) Applicant: Brett J. Lemire, Elk Grove, CA (US)

(72) Inventor: Brett J. Lemire, Elk Grove, CA (US)

(*) Notice: Subject to any disclaimer, the term of this patent is extended or adjusted under 35 U.S.C. 154(b) by 34 days.

(21) Appl. No.: 15/647,246

(22) Filed: Jul. 11, 2017

(51) Int. Cl.
*A63B 23/02* (2006.01)
*A63B 26/00* (2006.01)
*A63B 71/06* (2006.01)

(52) U.S. Cl.
CPC ........ *A63B 23/0244* (2013.01); *A63B 26/003* (2013.01); *A63B 71/0622* (2013.01); *A63B 2071/0633* (2013.01); *A63B 2071/0652* (2013.01)

(58) Field of Classification Search
CPC .......... A63B 21/4037; A63B 21/00047; A63B 21/40; A63B 21/4023; A63B 23/02; A63B 23/0244; A63B 26/00; A63B 26/003; A63B 69/0057; A63B 71/0036; A63B 71/06; A63B 71/0619; A63B 71/0622; A63B 2071/0602; A63B 2071/0647; A63B 2071/065; A63B 2071/0652; A63B 2071/0658; A63B 2071/0694; A63B 2210/00; A63B 2210/50; A63B 2225/09; A63B 2225/093; A63B 2225/12
See application file for complete search history.

(56) References Cited

U.S. PATENT DOCUMENTS

| 1,484,390 | A | * | 2/1924 | Gibbs | A63B 69/3667 283/115 |
| D190,241 | S | * | 5/1961 | Miller | D21/792 |
| 3,009,268 | A | * | 11/1961 | George, Sr. | A63D 1/00 434/249 |
| 3,210,079 | A | * | 10/1965 | Tryon | A63D 5/00 359/873 |
| 3,317,208 | A | * | 5/1967 | Birkle | A63D 5/00 434/249 |
| 3,611,591 | A | * | 10/1971 | Light | A63B 24/0003 434/252 |
| 4,805,913 | A | * | 2/1989 | Bott | A63B 69/3667 273/DIG. 30 |
| D335,696 | S | * | 5/1993 | Byers | D21/792 |
| 5,590,882 | A | * | 1/1997 | Todd | A63B 69/3623 473/218 |
| 5,603,617 | A | | 2/1997 | Light | |

(Continued)

OTHER PUBLICATIONS https://www.youtube.com/watch?v=hYxC4dV8IV4, published Aug. 30, 2013, last visited Nov. 30, 2018.*

*Primary Examiner* — Gary D Urbiel Goldner
(74) *Attorney, Agent, or Firm* — James M. Ritchey (57) ABSTRACT

A body postural analysis and corrective exercise mat and mirror for utilization in a process of evaluating and correcting, through exercise, a user's posture, wherein the mat includes a planar surface that displays an analysis and exercise region that is delineated by a front border, a rear border, and two opposing side borders and a grid matrix formed onto the mat surface, wherein the grid matrix has foot placement markings employed by the user to establish a reference alignment position, a rear alignment block located near the rear border, and a central axis reference line with a plurality of mirror image reference bands that extend from near the front border to near the rear border.

6 Claims, 3 Drawing Sheets

(56) References Cited

U.S. PATENT DOCUMENTS

| | | | |
|---|---|---|---|
| 5,842,931 A | 12/1998 | Payne | |
| 6,387,013 B1 | 5/2002 | Marquez | |
| D472,288 S * | 3/2003 | Grabowski | D21/792 |
| 6,592,376 B1 | 7/2003 | Carpenter | |
| D509,873 S * | 9/2005 | Dias | D21/792 |
| 7,108,635 B2 | 9/2006 | Howlett-Campanella | |
| 7,186,184 B2 * | 3/2007 | Buck | A63B 69/3661 |
| | | | 473/218 |
| D540,603 S * | 4/2007 | Stern | D6/591 |
| D621,454 S * | 8/2010 | Ohara | D21/662 |
| 7,819,777 B1 * | 10/2010 | Service | A63B 21/4037 |
| | | | 482/140 |
| 8,096,923 B2 | 1/2012 | White | |
| 8,235,870 B2 * | 8/2012 | Hamilton | A63B 71/0622 |
| | | | 434/247 |
| 8,499,383 B1 | 8/2013 | Ungaro | |
| D699,980 S * | 2/2014 | Tamayo | D6/589 |
| 8,794,975 B2 * | 8/2014 | Davey | A63B 23/0244 |
| | | | 434/236 |
| 8,961,372 B2 | 2/2015 | Hasta | |
| 9,241,589 B2 * | 1/2016 | Saltzman | A63B 23/035 |
| 2001/0034288 A1 * | 10/2001 | Howlett-Campanella | |
| | | | A63B 21/4037 |
| | | | 482/23 |
| 2003/0017915 A1 | 1/2003 | Prinzmetal | |
| 2004/0009845 A1 * | 1/2004 | Johnson | A63B 23/0464 |
| | | | 482/41 |
| 2004/0214692 A1 | 10/2004 | Koenig | |
| 2007/0243944 A1 * | 10/2007 | Paukune | A63B 24/0003 |
| | | | 473/267 |
| 2008/0096183 A1 * | 4/2008 | Cotran | A63B 71/06 |
| | | | 434/428 |
| 2008/0102970 A1 * | 5/2008 | Park | A63B 24/0003 |
| | | | 473/180 |
| 2009/0239724 A1 * | 9/2009 | White | A63B 23/0244 |
| | | | 482/142 |
| 2011/0035878 A1 * | 2/2011 | Rouse | A47G 27/0237 |
| | | | 5/417 |
| 2011/0111926 A1 * | 5/2011 | Goranson | A63B 6/00 |
| | | | 482/23 |
| 2012/0317719 A1 * | 12/2012 | Ng | A47G 27/0237 |
| | | | 5/417 |
| 2013/0180048 A1 * | 7/2013 | Saltzman | A63B 23/035 |
| | | | 5/417 |
| 2014/0237718 A1 * | 8/2014 | Burch | A63B 21/4037 |
| | | | 5/417 |
| 2015/0100251 A1 * | 4/2015 | Solinsky | G01C 21/005 |
| | | | 702/33 |
| 2015/0243185 A1 | 8/2015 | Purdy | |
| 2016/0136476 A1 * | 5/2016 | Saltzman | A63B 23/035 |
| | | | 5/417 |
| 2016/0346660 A1 * | 12/2016 | Johnson | A63B 69/3661 |
| 2017/0100630 A1 * | 4/2017 | Mizuno | G06F 19/3481 |

* cited by examiner

BODY POSTURAL ANALYSIS AND CORRECTIVE EXERCISE MAT AND METHOD OF UTILIZATION

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This technology pertains generally to a specifically configured mat with grid markings that is utilized in the analysis and correction of a person's body posture. More particularly to a body posture analysis and correction exercise mat that has alignment grid marking that is employed in connection with a mirror that reflects both a user's image and the alignment mat markings to permit an analysis of the user's postural alignment and may be utilized by only the user or the user with directions from a qualified medical professional.

2. Background Discussion

Various exercise mats exist for padding individuals against hard surfaces and indicating general orientation positions on the mat for stretching. Examples of such simplistic mats include: U.S. Pat. Nos. 6,387,013; 6,592,376; 7,108,635; 8,096,923; and 8,499,383; 8,961,372 and US Publication Nos.: 2003/0017915 and 2004/0214692.

Two US patents (U.S. Pat. Nos. 5,842,931 and 5,603,617) present golf swing training devices that utilize either a head-band mounted mirror or a combination mirror and video monitor in conjunction with either a background pattern or a mirror-to-video comparison means, respectively.

US Publication No.: 2015/0243185 discloses a mirror in which the mirror has weight lifting alignment markings and magnetic markers that an athlete employs to learn proper form for weight lifting routines. A pair of light sources are connected to a bar used by the athlete so that the athlete may easily track the bar's movement in the mirror.

BRIEF SUMMARY

An aspect of the technology is a body postural analysis and exercise correction mat that has a grid matrix formed of its upper surface.

Another aspect of the technology is a body postural analysis and exercise correction mat that has a grid matrix formed of its upper surface that is employed by a user in conjunction with a mirror that reflects body alignment positions.

A still further aspect of the technology is a body postural analysis and exercise correction mat that has a grid matrix formed of its upper surface that is employed by a user in conjunction with a mirror that reflects body alignment positions and a healthcare professional utilizes the mat and mirror to analyze the user's posture and to provide corrective exercises to the user.

Yet still a further aspect of the technology is a body postural analysis and exercise correction mat that has a grid matrix formed of its upper surface that is employed by a user in conjunction with a mirror that reflects body alignment positions in which the mat is printed or otherwise marked on a floor surface or formed on a flexible mat material that may be rolled or folded for easy transport.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only.

DETAILED DESCRIPTION

Figure 1:
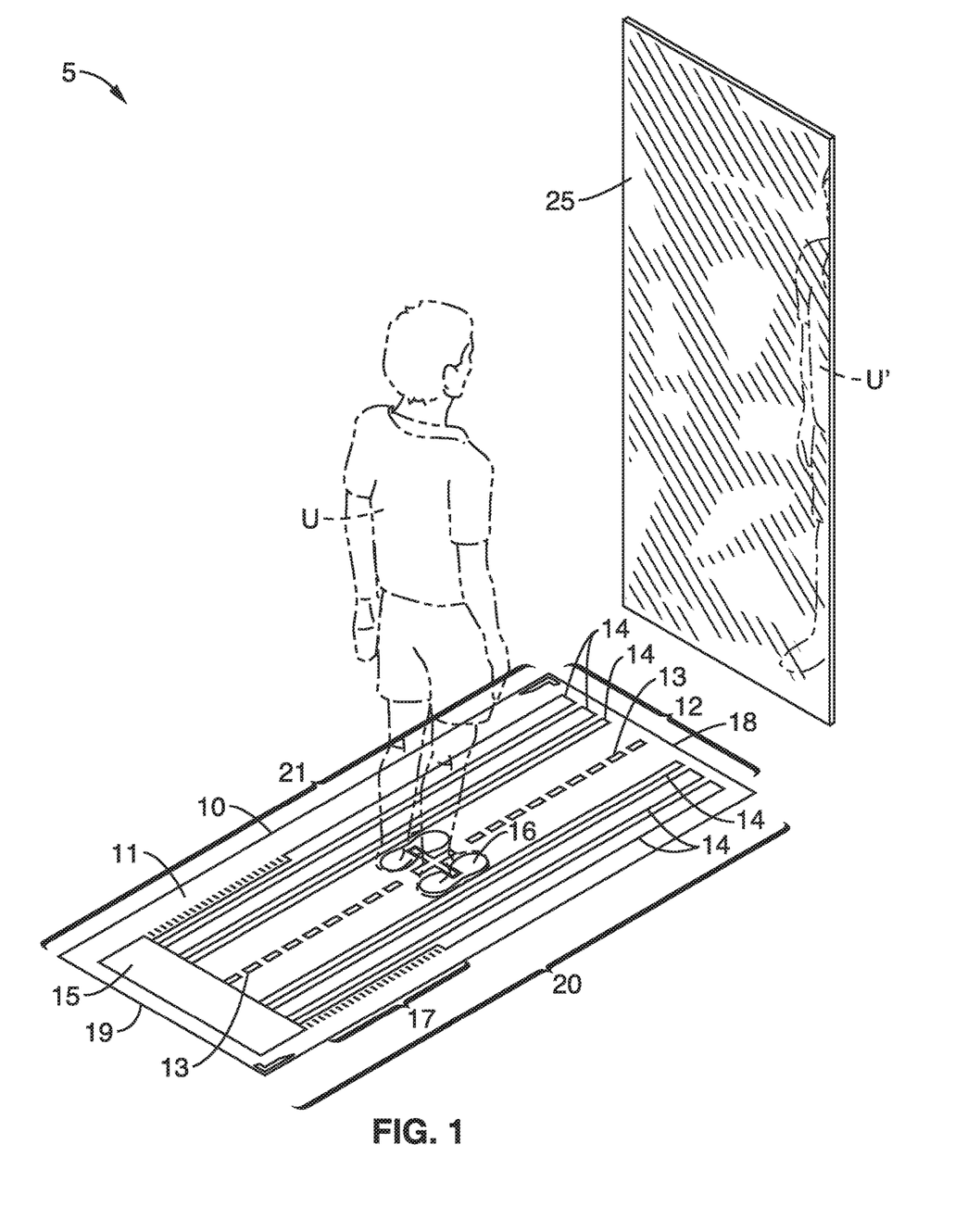
FIG. 1 is perspective view of a user standing on a subject posture alignment mat that has grid matrix markings for determining the user's postural alignment by means of the user's reflection in a mirror.
Figure 2:
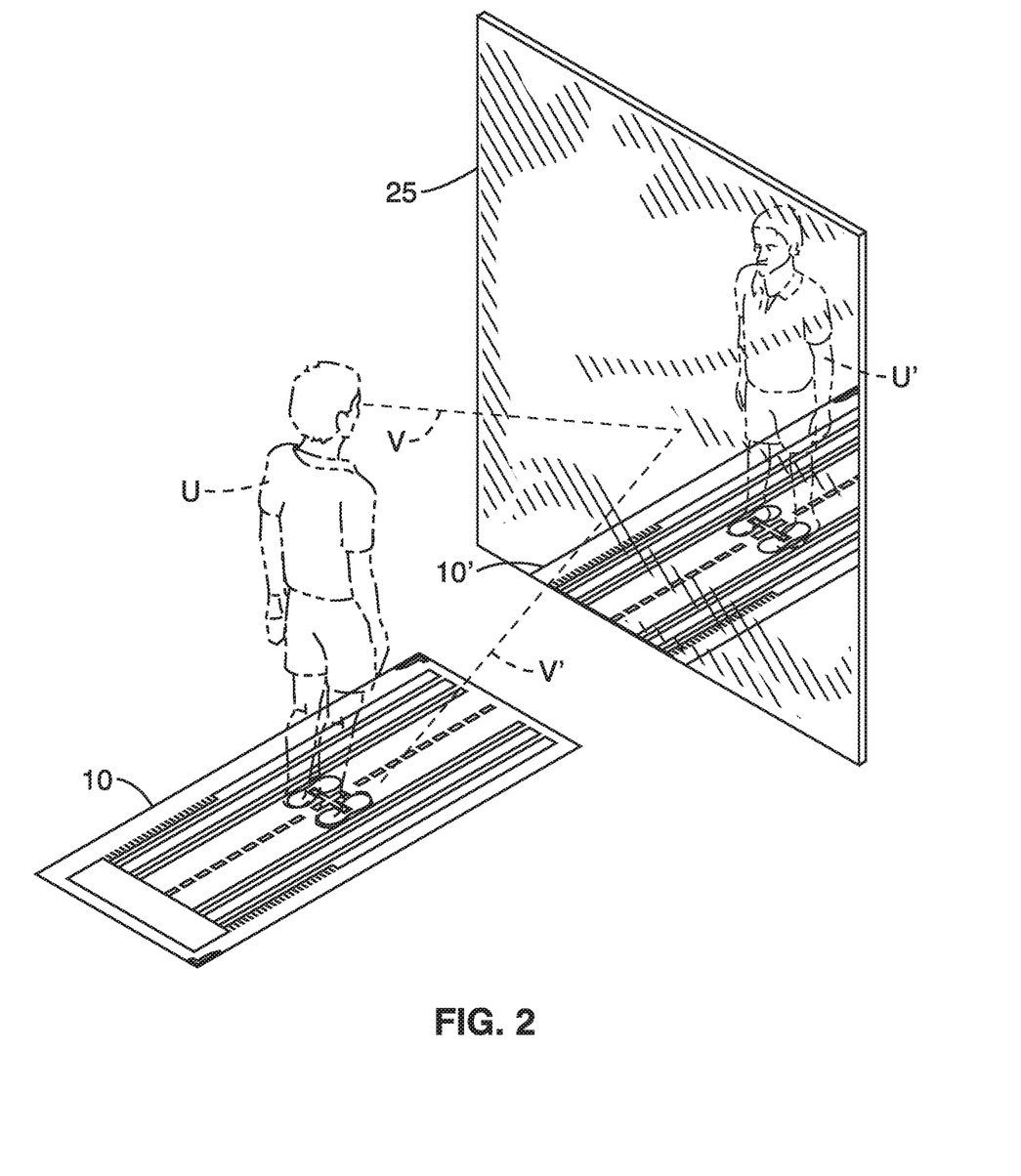
FIG. 2 is perspective view showing the user employing the mirror's reflection of both the user and the subject postural analysis and correction mat's grid markings in which various postural body positions are compared against the grid markings.
Figure 3:
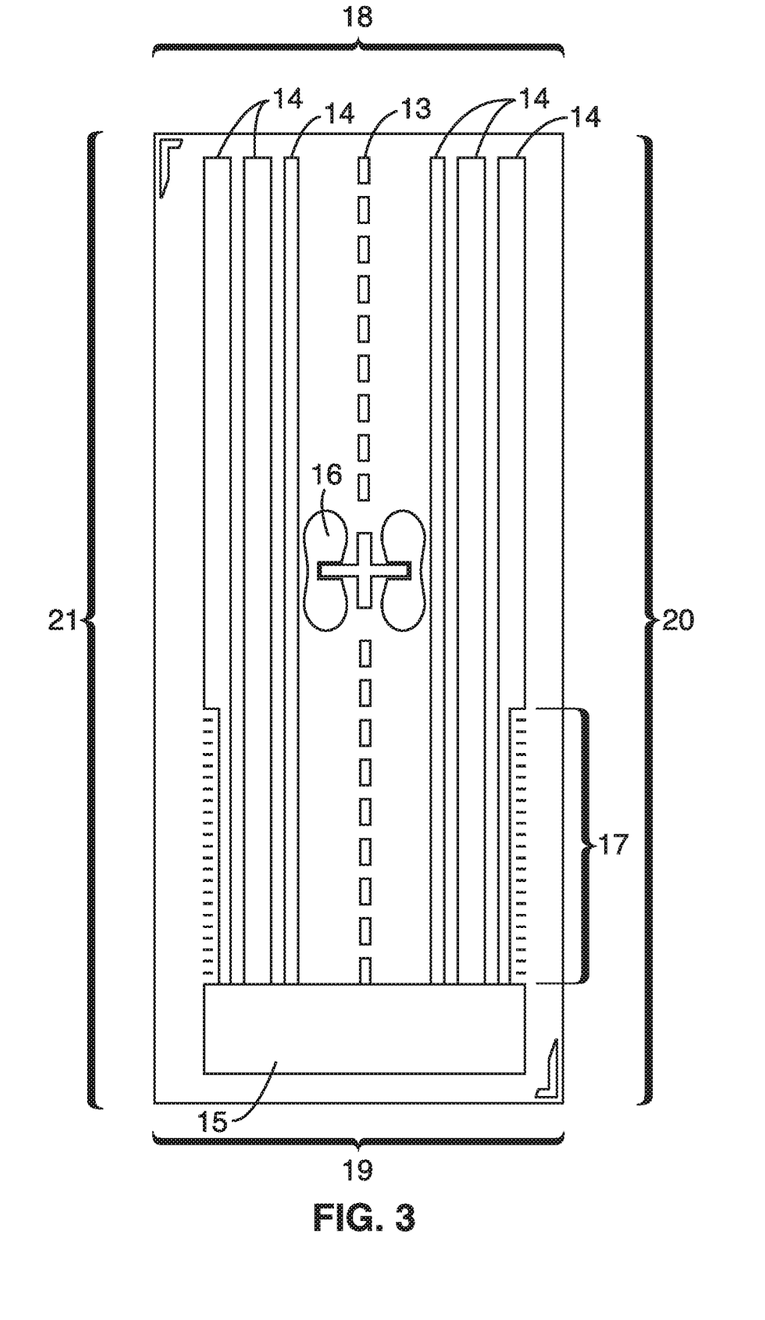
FIG. 3 is a top view of the subject postural analysis and correction mat showing the various upper surface grid markings including the two central foot placement zones and a series of parallel alignment bands, stripes, or lines.

Referring more specifically to the drawings, for illustrative purposes the present technology is embodied in the apparatus generally shown in FIG. 1 through FIG. 3. It will be appreciated that the apparatus may vary as to configuration and as to details of the parts, and that the method may vary as to the specific steps and sequence, without departing from the basic concepts as disclosed herein.

Normally, the subject technology is employed by either a user U or a user U in conjunction with a qualified healthcare professional. Once the healthcare professional has instructed/trained the user U in the utilization of the subject technology then the user U may employ the subject technology in postural analysis and corrective exercises without the presence of the healthcare professional.

FIGS. 1, 2 and 3 show the subject technology 5. Included in the subject technology 5 are a postural analysis and correction exercise mat 10 (see FIG. 3 for details) and an associated mirror 25. A user U is shown standing on the mat's 10 upper surface 11, with the user's reflection U' shown in the mirror 25. The mat's upper surface 11 includes various calibration/alignment grid matrix markings 12. The grid matrix markings 12 comprise a central axis line 13 (dashed or otherwise designated), feet placement regions 16, stripes, or bands 14 that run the length of the mat's upper surface 11 (mirror imaged about the central line 13 lines), and a rear reference zone 15. The lines, stripes, or bands 14 are symmetrically positioned (mirror-imaged) about a central axis line 12 and are utilized in alignments utilizing the user's U reflection in the mirror 25.

Additional calibration markings 17 are generally positioned along the outer sides of the outermost lines, stripes, or bands 14. These calibration markings 17 are utilized to measure the extent of the user's U body position during selected stretching maneuvers.

The mat 10 may be a separate unit, preferably of an elongated configuration/shape, fabricated from any suitable material including natural substances or synthetic polymeric substances and the like that may be rolled or folded into an easily transported form or printed on a floor or carpeted area. By way of example and not by way of limitation, the mat 10 usually comprises a rectangular shape with a front edge 18 and a rear edge 19, with opposing side edges 20 and 21. The gird markings 12 are imprinted on the surface of the mat 10 by standard means.

FIG. 2 shows the user U standing on the subject mat 10 and the user's reflection U' in the mirror 25 that is positioned so that the user U may see (via user-to-mirror viewing V and mirror-to-user/mat reflection images) the reflection of the subject mat 10' and the user's U body alignment in the mirror 25 reflection V'.

FIG. 3 shows the subject mat 10 with the various grid matrix markings 12 inscribed on the upper surface of the mat 10. The grid matrix markings 12 are employed by the user U in various postural analysis procedures and corrective exercises (see below for detailed procedures and exercises).

For use of the subject technology, the user U initially places their feet on the feet placement regions 16. Next, the user U performs postural analysis movements and/or corrective exercises with or without the direction of a healthcare profession.

Methods and Procedures for Measurements and Exercises

The following are basic descriptions of the postural analysis or procedural assessments and corrective exercises using the subject mat 10 and mirror 25. The technology 5 is utilized by either a lone user U or, preferably, the user U in cooperation with a healthcare professional. The healthcare professional normally trains the user U to employ the subject technology to be utilized at home or in any suitably convenient location.

Key Terms and Abbreviations

Center of gravity—COG
Center of mass—COG
Base of support—BOS
Gravity Line—GL

Chin-sternum and zipper-line—referred to as the CSZ-line
4-corners—Right and left shoulders and hips forming a visual "rectangle" and or 4-corners Procedure 1: Mirror test 1—Front view standing posture in front of the mirror.

Purpose—The ability to assess standing upright posture facing a full-length mirror.

Steps in Process—The patient-user faces forward on the grid matrix facing the wall mirror; standing in a neutral or normal posture with arms to the side, over the "+" with feet equal distance apart from each other and on top of the foot marker region 16.

Evaluation for Mirror Test 1 Sagittal Plane: (CSZ & 4-Corners):

a. The patient-user can visually see their posture forward facing posture in the mirror, and observations and comments relative to the grid matrix lines by the healthcare professional.

b. In this position, the patient-user cannot see the spine in this view, the alignment of chin-sternum and zipper relative to the dash-line on the floor grid matrix can be used as a midline reference for the spine and symmetry of posture.

c. Under ideal posture the spine should straight and CSZ-line should be a mirror image of spine. Any deviation of CSZ-line to the grid matrix lines can help the user understand the mirror deviations that could exist in the spine.

d. The CSZ-line also separates the body into right and left halves. As described below the "4-corners can be divided into right shoulder and hip relative to the CSZ-line and visa versa.

e. The "4-corner's" refers to the visual orientation and symmetry body regions looking for asymmetry of right-left shoulder line and the right-left hip line.

Assessing Skeletal Geometry or Deviations from Neutral Posture

Terms to describe observations of regional and global posture in sagittal plane are now listed.

Chin-sternum and Zipper-line (CSZ-line)—imaginary midline on the front of the body that connects center of nose-chin to midline or sternum and navel or zipper of clothing if present of user.

The alignment of the "4-corner's" relative to the CSZ-line and it's orientation on the grid matrix.

Visual observation & orientation of right & left shoulder-lines.

Visual observation & orientation of right & left hip lines.

Visual observation & orientation of right shoulder & right hip regions relative to the CSZ-line.

Visual observation & orientation of left shoulder & left hip regions relative to the CSZ-line.

Tilt—a portion of the body is tilting off the vertical axis (CSZ); example: head tilted relative to ribcage; ribcage to the pelvis. Foot tilt—medial or lateral (pronation/supination). Medial tilt to the scapula (upward rotation), lateral tilt (downward rotation).

Bend—refers to vertebral tilts in the spine (cervical, thoracic, lumbar spine); only refers to the spine. Different then the regional tilts.

Shift—refers to translation of body regions: COG or pelvis has moved relative to the COM or ribcage.

Rotate—a deviation in transverse plane deviation: scapula protracts (or outwardly or laterally rotates).

Procedure 2: Mirror test 2—Side view standing in front of the mirror.

Purpose—the ability to assess the GL in standing upright posture from the side-view in a full-length mirror.

Steps in process—The patient-user faces perpendicular or 90 degrees from MT-1 position standing on the grid matrix; standing in a neutral or normal posture with arms to the side, over the "+" with feet equal distance apart from each other and perpendicular over the top of foot markers.

Evaluation of Mirror Test 2 Frontal Plane: (GL)

Assess Skeletal Geometry (Exam Cephalo-Caudal)

Terms to describe observations of regional and global posture in frontal plane are now listed.

Tilt—anterior tilt or the head, ribcage or pelvis (ASIS to the femoral line).

Bend—series of vertebral segmental tilts (I.e. forward head or kyphosis in the thoracic spine).

Shift—refers to translation or body regions from the A-P directions:

COG or pelvis has moved on the COM or ribcage. The head or neck may or may not be posturally reacting.

Four pelvic types with A-shift or P-shift—relative to the ankle & foot (BOS) and A-tilt or P-tilt—relative to the femoral line.
1. A-shift+A-tilt—both going anterior—"open-scissors".
2. A-shift+P-tilt—very common.
3. P-shift+A-tilt—pediatrics.
4. P-shift+P-tilt—the "flat back" posture.

Rotate—transverse plane deviation: "observe by holding the PSIS and aligning to the heels, then looking down the spine like a gun-barrel will give you side of posterior rotation "what is the primary rotation of the spine by looking at the T-L junction: Ask them to look over their shoulder, they primary way will be the predilection on the direction they prefer to rotate towards. Name for what happens to the front structure (i.e. the R. ribcage rotates forward & too the left). A R. ribcage+L. pelvic rotation—is very common.

Procedure 3: Romberg and Sharpened Romberg Test—

Purpose—Assess balance and truncal stability based or directional sway in the body for purpose of fall prevention and body stability.

Steps in Process— a. The patient is asked to remove his shoes and stand with his two feet together over the grid/foot marker region. The arms are held next to the body or crossed in front of the body.

b. Instruct patient to first stand quietly with eyes open and then with eyes closed. Patient attempts to maintain their balance. Note—For safety purposes, the evaluator stands close to the patient-user on the grid matrix to prevent injury if a fall were to occur.

Sharpened Test Variation—Start with the feet in heel-to-toe position, with one foot directly in front of the other. The patient crosses his arms over his chest, and the open palm of the hand lies on the opposite shoulder.

Evaluation—Both versions of the Romberg test are positive when the patient is unable to maintain balance with their eyes closed. Losing balance can be defined as increased body sway, placing one foot in the direction of the sway/fall or even falling. The feet are in tandem stance, which means the big toe of the back foot is touching the heel of the front foot. The test should last a minimum of 30 seconds, and if the client makes it to 60 seconds, the test can be terminated. Repeat with the opposite foot in front, and be sure to note any side discrepancies.

Procedure 4: Dynamic or Walking Romberg Test—

Purpose—To assess proprioception and vestibular function while walking on the grid matrix with eyes-closed.

Steps in process— a. Patient stands on solid plate with feet same distance apart as on the black foot markers over the "+".

b. Arms crossed across the chest with palms on shoulders.

c. With the eyes-closed they walk forward 6-10 steps or until clinician instructs them to stop and remain in that position for measurement.

Evaluation a. Assess for patient loss of body alignment, balance and coordination.

b. Assess for pelvic shift, buckling on support limb or Trendelenburg sign.

c. Assess for ankle, knee and hip instability.

d. Assess for disorientation and dizziness.

e. Assess for stepping on or over the dash-line and direction of preferential sway or drift along the grid matrix (i.e. drifts right or left etc.).

Procedure 5: Fukuda Step Test—

Purpose—To assess labyrinthine function via vestibule-spinal reflexes during stepping function with the eyes closed.

Steps in process—

The patient is asked to remove his shoes and stand with his two feet together over the foot marker region. The arms are stretched out in front of the body, with the eyes-closed, the patient-user steps in place for 50 to 100 steps, then stops and remains in place for measurement.

Evaluation— a. Assess the amount of rotation and displacement measured after taking 50 or 100 steps in place with the eyes closed and with arms outstretched at 90°.

b. Note: Additional marks on the grid matrix should be identified such as 2 concentric circles with radii of 0.5 and 1.0 m, and divided into angles of 30°.

c. Assess how displacement forward or backward and side to side relative to the 30° angles over 0.5-1 m circles.

d. If you have taken only 50 steps, then an angle of 30 degrees or more may indicate vestibular weakness to the side your body deviated.

Procedure 6: Squat Test—

Purpose—Assess the quality of movement during a basic squat pattern.

Steps in Process— a. Stand over the black foot markers ("+") with feet equal distance apart.

b. Step-out to the 2-inch width parallel line that reflects your hip measurements.

c. Perform an athletic type squat keeping your heels down and pushing your hips back. Limit the cueing of the patient to observe their natural movement.

Evaluation— a. Assess the lower extremity for compensations or restricted movement at the ankle, hip, thoracic spine, and shoulder.

b. Assess for lower extremity for instability at the foot, knee, lumbo-pelvic region and trunk.

c. Assess whether the foot faces forward and knees track on the parallel lines of the grid matrix over the feet, but not past toes.

d. Assess the hip-hinging backwards as the knee hinges.

e. Assess whether the zipper line shifts to the left or right, if one pelvis drops lower than the other.

Procedure 7: Single Leg Stance Test—

Purpose—To assess the alignment, balance and coordination of the body in the single leg stance position, first eyes-open (EO) first, and followed by eyes-closed (EC).

Steps in Process— a. Stand facing the mirror in a neutral "upright" body posture with feet directly over the "+" on the foot markers, keeping your arms relaxed along the sides of the body.

b. Cross the arms on the chest with palms on the shoulder.

c. Lift one leg up to 90 of hip and knee flexion, and hold.

d. Repeat on the opposite side.

Evaluation— a. EO—assess SLS for; pelvic shift towards parallel line, loss of balance, lower extremity instability at the foot, ankle, knee hip and trunk.

b. EO—timed SLS.

c. Re-assess with EC, and timed.

d. Compare results bilateral.

Procedure 8: Standing—Bilateral Overhead Reach Test BORT—

Purpose—The BORT, assesses the quality, symmetry and level of discomfort of the patient's ability to actively disassociate and control spinal positions in the lumbo-pelvic, thoraco-lumbar and cervico-thoracic regions, from the upper extremity (i.e.—scapula, gleno-humeral joint, elbow and wrist) while performing a bilateral overhead reach movement.

Steps in Process— a. Stand facing the mirror in a neutral "upright" body posture with feet directly over the "+" on the foot markers, keeping your arms relaxed along the sides of the body.

b. The patient lifts arm slowly overhead into shoulder flexion, pause briefly and return the arms to the side. Repeat several attempts.

Evaluation—

Evaluator/healthcare provider—stands behind the patient and off the grid matrix to assess patient-user.

a. Observe for symmetry, ease and range motion during the limb movement.

i. $1^{st}$ phase—assess the "concentric" elevation phase of the arms—normal ROM: flexion of shoulders to 160°-180° with the GH contributing up to 120° & scapula contributes up to 60° on upward rotation.

ii. $2^{nd}$ phase—assess the "end-range" or pause and transition into the lowering phase.

iii. $3^{rd}$ phase—assess the "eccentric" lowering phase of the arms.

b. Assess compensations on elevation phase of the arms—observing the lumbo-pelvic region (shift, sway, or arching of the low back—i.e. leaning back).

c. Assess thoracic spine motion (extension, scapula-thoracic retraction and glenohumerual joint motion—scapular "sticking or hiking" signs of compensations).

d. Observe and sasses the elbow and wrist for flexion and extension on the elevation phase of the arms.

Procedure 9: Plank "Core" Test—

Purpose—To assess core stability in the plank position.

Steps in process— a. Assume a quadruped position placing hands and knees over the top of one-set of the parallel lines, and keep your navel over the top portion of the "+".

b. Middle finger of hand, kneecap, and toes should be aligned on the grid matrix lines. The patient user lifts the knees off the floor into a full plank (hands, feet & toes in a vertical "neutral" start position).

c. From the plank position, the patient is instructed to lift the right then return to start, followed by the left in the same way.

d. The arms can also be lifted in the same fashion.

e. The opposite arm and leg can be lifted, and repeated on the opposite diagonal.

Evaluation—(assess for a stable position of the trunk as either a leg, arm or diagonal arm and leg are lifted from the floor).

a. Assess for compensatory shift of the pelvis on the support leg when the opposite leg is lifted.

b. Assess for a compensatory drop of the pelvis, head, arching or rounding of the back during the lift phase of the extremity.

c. Assess for alignment, symmetry & height of the leg being lifted.

d. Assess for alteration of foot position from neutral start position.

e. Assess for compensation in the shoulder blades (winging, retraction, protraction or shifting from neutral start position).

f. Observe several reps to monitor the affects of fatigue on motor performance.

Procedure 10a: Crawling Assessment—

Purpose—To assess timing and symmetry of crawling in either

"Traditional" hands and knees position or in a more advanced "Bear-crawl" position (hands and feet).

Steps in process— a. Assume a 4-point kneeling or quadruped position placing hands and knees over the top of one-set of the parallel lines, and keep your navel over the top portion of the "+".

b. Middle finger of hand, kneecap and toes should be aligned on the grid matrix lines.

c. Begin to crawl forward to the front of the grid matrix and then backwards to start position.

Evaluation—(assessment is made crawling forward and backwards).

a. Assess the alignment of the hands and knees relative to the parallel lines (i.e. lands inside or outside of the lines).

b. The patient-user lifts hand and opposite knee off the grid matrix and steps forward, assess the timing of the hand-knee lift for discrepancy for being in-sync or out-of-sync.

c. The patient-user steps forward with the hand and opposite knee.

Assess the timing, amplitude and placement of the stepping forward extremities. Use the numerical system on the dash-line to measure displacement of the hands and knees, compare ipsilateral and bilateral.

d. Assess for excessive pelvic shift on support leg, and hip dysfunction on the stepping forward leg.

Procedure 10b: Bird-dog Assessment—

Purpose—To assess core stability while executing upper extremity, lower extremity and contralateral upper and lower extremity movements in the 4-point kneeling (quadruped position).

Steps in Process— a. Assume a 4-point kneeling or quadruped position placing hands and knees over the top of one-set of the parallel lines, and keep your navel over the top portion of the "+".

b. From a neutral spine position, lift one arm forward into shoulder flexion and return to start position. Repeat on the opposite side.

c. Diagonal Extremity Lift Position—From a neutral spine position, lift on leg back into extension and return to start position. Repeat on the side.

d. Diagonal Elbow & Knee Touch—1$^{st}$ part—From a neutral spine position, simultaneously lift one knee and hand off the grid matrix line and hold in diagonal leg extension and shoulder flexion. 2$^{nd}$ part—from the diagonal extended and lift position, touch the Elbow and Knee of the reaching limbs underneath the body, then return to start position. Repeat on the side.

Evaluation— a. Assess core stability and extremity mobility and for compensatory movements in the pelvis, trunk and shoulder blades during the lift phase of each extremity.

b. During Diagonal Extremity Lift Position, assess core stability, core stability and extremity mobility during combined diagonal movement patterns over the grid matrix.

c. Assess core stability and extremity mobility and for compensatory movements in the pelvis, trunk and shoulder blades during the stability phase as the Elbow & Knee touch diagonally underneath the body while over the grid matrix.

Procedure 10c: Bear Crawl (Hands & Toes)—

Purpose—To assess core stability while executing upper extremity, lower extremity and contralateral upper and lower extremity movements in the 4-point hands & toes position on the grid matrix (quadruped position).

Steps in Process— a. U assumes a four-point kneeling position on the Grid. Hand, knee and foot placement can be on either the 2$^{nd}$, 3$^{rd}$ or 4$^{th}$ parallel line depending on the size of the U.

b. Lift both knees off the floor with hips higher than the shoulders and balance in that position. Lift one hand off the floor, hold and balance for 5-10 seconds (or desired time by U or practitioner). Repeat on the opposite side. Lift one of the feet off the floor, hold and balance for 5-10 seconds (or desired time by U or practitioner). Then lift opposite extremities of the floor (e.g. R. hand and L. foot), hold and balance for 5-10 seconds (or desired time by U or practitioner).

Evaluation— a. Assess for compensatory shift of the pelvis on the support leg when the opposite leg is lifted.

b. Assess for a compensatory drop of the pelvis, head, arching or rounding of the back during the lift phase of the extremity.

c. Assess for alignment, symmetry & height of the leg being lifted.

d. Assess for alteration of foot and ankle position from neutral start position (e.g. collapse into pronation, supination, eversion etc.).

e. Assess for compensation in the shoulder blades (winging, retraction, protraction or shifting from neutral start position).

f. Observe several reps to monitor the affects of fatigue on motor performance.

Procedure 11: Standing Differentiated Hip Rotation—

Purpose—To assess whether one lower extremity can remained in support with the pelvis, trunk and opposite lower extremity can rotate away.

Steps in Process— a. Face mirror and stand on the foot marks, step-out onto a set of parallel lines with left foot on left line and right foot on right line.

b. Step into a "staggered stance" with one foot forward and other foot back onto the parallel lines (approximately same width of your squat stance). Use symmetrical distance on dash-line between the front and back foot to maintain a metric assessment.

c. Place hands together in front of chest. CSZ-line is in alignment with the dash-line, entire foot in alignment with the parallel lines.

d. Lift the heel of the back foot off the floor, and shift your body weight forward onto the front leg.

e. Rotate your body towards the back foot approximately 45° allowing the back foot to pivot on the ball of the foot.

f. Return to start position. Repeat on the other both sides.

Evaluation— a. Assess for general and specific alignment, balance and control issues in the staggered stance position.

b. Assess whether the patient-user can disassociate movement of the pelvis and hip on the front leg.

c. Assess whether the lower kinetic chain on the front leg compensates during backward and forward rotation (valgus collapse at ankle, tibia, and knee).

d. Assess for trunk lean and pelvic shift. Trunk and shoulders should not disconnect from the pelvis during the movement.

e. asses right versus left staggered stance patterns.

Procedure 12: Single Leg Stance—"Sliders Exercise"—

Purpose—To exercise on the grid matrix in a "modified" single leg stance position.

Steps in Process— a. The patient-user stands over the foot markers ("+") with feet equal distance apart.

b. Place a Val-slide (i.e. plastic furniture mover) underneath one of the feet and on top of the grid matrix (example—under the right foot).

c. Backwards slide—Shifting some of your weight to the left lower extremity, slide the right foot back several dash marks, and return to start.

d. Forwards slide—Shifting weight to the left leg, slide the right foot forward several dash marks, and return to start.

e. Repeat on the opposite side.

Evaluation— a. Assess for body alignment, balance and coordination of the stance leg and sliding backwards and forwards leg.

b. Assess for hip shift backwards or side to side.

c. Assess alignment of sliding foot relative to the track created by the dash-line and the 2$^{nd}$ parallel line.

d. asses the amount of dashes forward and backward, compare for symmetry.

Procedure 13: Thoracic & Hip Mobility—

Purpose—To assess the side to side mobility of the thoraco-pelvic soft-tissues and joints.

Steps in Process— a. The patient-user stands over the foot markers ("+") with feet equal distance apart, arms crossed on the chest with palms on the shoulders.

b. Keeping your shoulders level and stationary, shift your hip either right or left towards 2-inch parallel line adjacent to the foot marker. Repeat in the opposite direction.

Evaluation— a. Assess for restriction, excess mobility or compensatory movement in the torso, shoulders or lower extremity.

Procedure 14: Tall Kneeling Step Through Lunge Pattern—

Purpose—To assess the mobility, stability and coordination in the trunk, pelvis and hips during single limb support combined with stepping forward hip flexion.

Steps in Process—
a. The patient-user kneels over the foot markers ("+") with knees equal distance apart, arms crossed on the chest with palms on the shoulders.
b. Shift weight onto the left leg, and bring the right leg through to the lunge position. Repeat several repetitions, and repeat sequence on the opposite side.
Evaluation—
a. Assess for compensatory trunk lean to assist in lifting the pelvis and the stepping forward leg off the floor.
b. Assess whether the stepping forward leg "sweeps" through without excess circumduction.
c. Compare the movement qualities between the left and right sides.

Procedure 15: Hurdle Step (FMS Version HS on the Grid Matrix—
Purpose—To assess the mobility, stability and coordination of the FMS hurdle step screen.
Steps in Process—
a. Stand in the middle of the Grid and perpendicular to outer edge of one of the black lines (facing inward to the Grid with toes next to the outer edge of the black line. Cross the arms on the chest with palms on the shoulders, eyes straight ahead. If using FMS method, use the dowel across the shoulder as described in the FMS screening method. Place a barrier either physical or a light source (laser beam) at the level of the tibial tuberosity and have the U step over the barrier with one leg, touch the floor with heel and return to the start position. Repeat on the opposite side.
Evaluation—
Observe for inability to perform the movement, touching the barrier with the leg being lifted, loss of balance, change in posture (i.e. trunk lean) such as the dowel doesn't stay parallel in the start position, compensatory movement at the hip, leg or ankle. Difficulty transitioning from the heel touch back to the start position. Comparable differences between the left and right side.
Alternative method would be to use an artificial source such as from a light laser that would shine superimposed to the outer line of the Grid at the level of the tibial tuberosity. The light source would replace the physical barrier, if the U hits the light beam at any point in the screen, then it would be considered a "positive" finding just as with the physical barrier used in the FMS screen by Gray Cook, PT & Lee Burton Ph.D.
A. Use FMS scoring system if desired.

Procedure 16: Active Straight Leg-Raise (FMS Version ASLR on the Grid Matrix)—
Purpose—To assess the mobility and quality of movement during the ASLR.
Steps in Process—
The U lays perpendicular to the Grid (facing inward at the level of "+") with the knees superimposed over the outer black line and arms down to the side of the body. The test is performed as described in the FMS protocol for the ASLR, however, it's perform over the Grid. Legs are together, toes are dorsiflexed, and one leg is lifted off the floor to end-range of motion and assessed. Leg is lowered and repeated on the opposite side.
Evaluation—
a. Assess how many dash marks past the support knee on the floor and towards the hips does the heel travel.
b. Compare right and left ASLR.
c. Use FMS scoring system if desired.

Procedure 17: Pitchers Stride—
Purpose—to assess the mobility, stability and length of a pitchers stride.

Steps in Process—
a. Stand on the logo plate in the right or left handed pitchers position.
b. Perform a simulated pitch on the grid matrix.
Evaluation—
a. Assess for mobility and stability of the lower kinetic chain, trunk and shoulder.
b. Assess the alignment and landing of the lead foot.
c. Measure the length of the stride Procedure 18: Disassociation of Head, Thoracic & Lumbar Spine—"Up-Righting" Screen—
Purpose—To assess the ability upright the thoracic spine relative to the head and pelvis.
Steps in process—
a. Standing in mirror test 2 position, with malleolus of ankle super-imposed over the "+" and in-line with dash line. The knees, hips and shoulders are up-righted over the malleolus's onto GL, and remain in that position. The U attempts to upright or straighten the middle back without moving the hips or shoulders off of the GL.
Evaluation—
a. The observer observes in the mirror for the ability of the U to maintain the malleolus, knee, hip and shoulders, and center ear in contact with GL while attempting to upright the thoracic spine. Observe for compensatory movement of the knee, pelvis, lumbar spine, shoulders or head during the up-righting movement of the thoracic spine.

Procedure 19: Backwards Walking—
Purpose—To assess and measure the degree of hip extension with backwards walking
Steps in process—
a. Standing at front of the Grid closest to the mirror, the U crosses the arms on the chest and slowly walks backwards the full distance of the Grid.
Evaluation—The observer notes the quality of movement such as posture, balance, body sway, hip hiking, "fixated" or restricted movement, ease of movement, and the degree of hip extension relative the dash lines on the Grid. Such as the right leg step back one dash backwards while the left leg measured two, with restriction noted in the right pelvis, hip-hiking and loss of balance etc.

Procedure 20: The Overhead Deep Squat (FMS Version Deep Squat Movement)—
Purpose—To evaluate on the Grid, the quality of the Deep Squat
Movement pattern, which requires symmetrical mobility of the hips and shoulders functioning with a stable core.
Steps in process—
a. Depending the size of the U, they can stand on the either $2^{nd}$, $3^{rd}$, or $4^{th}$ parallel line for assessment. Toes facing forward and heels on the line, Grasp the dowel in both hands and place it on top of your head so your shoulders and elbows are at 90° degrees, raise the dowel up into the overhead position. Keep heels and feet in place, back straight, and perform a deep squat, hold in the bottom position for 1 second, then return to start position. Use up to 3 attempts.
b. Alternative method—no dowel, with hands clasped behind the head.
c. Perform same deep squat movement and return to start position.
Evaluation—
a. Use FMS assessment and scoring system if desired.
b. Assess foot, knee and entire lower extremity alignment or tracking during the movement pattern. Assess for heel lift or movement. Assess for correct trunk inclination or change in shoulder positions.

From the description herein, it will be appreciated that the present disclosure encompasses multiple embodiments which include, but are not limited to, the following:

1. A body postural analysis and corrective exercise mat for utilization in a process of evaluating and correcting a user's posture, wherein the mat comprises: (a) a substantially planar surface that displays an analysis and exercise region that is delineated by a front border, a rear border, and two opposing side borders; (b) a grid matrix formed onto said mat surface within said analysis and exercise region, wherein said grid matrix comprises: (i) foot placement markings employed by the user to establish a reference alignment position; (ii) a rear alignment block located proximate said rear border; and (iii) a central axis reference line and a plurality of mirror image reference bands that extend from proximate said front border to proximate said rear border.

2. The mat of any preceding or subsequent embodiment, further comprising a series of measurement hash marks on each of outer most mirror image reference bands proximate said rear border.

3. The mat of any preceding or subsequent embodiment, wherein said mat comprises a sheet of material that may be rolled or folded into a compact form for transport.

4. A body postural analysis and corrective exercise system for utilization in a process of evaluating and correcting a user's posture, wherein the mat comprises: (a) a mat having a substantially planar surface that displays an analysis and exercise region that is delineated by a front border, a rear border, and two opposing side borders; (b) a grid matrix formed onto said mat surface within said analysis and exercise region, wherein said grid matrix comprises: (i) foot placement markings employed by the user to establish a reference alignment position; (ii) a rear alignment block located proximate said rear border; and (iii) a central axis reference line and a plurality of mirror image reference bands that extend from proximate said front border to proximate said rear border; and (c) a mirror placed to reflect to the user both the user's image and the grid matrix, thereby allowing an analysis of the user's posture for use in conjunction with posture correcting exercises.

5. The system of any preceding or subsequent embodiment, wherein said mat comprises a sheet of material that may be rolled or folded into a compact form for transport.

6. A method for analyzing and correcting a user's postural alignment, comprising the steps: (a) placing a postural analysis and corrective exercise mat on a supporting surface, wherein said mat comprises: (i) a substantially planar surface that displays an analysis and exercise region that is delineated by a front border, a rear border, and two opposing side borders; (ii) a grid matrix formed onto said mat surface within said analysis and exercise region, wherein said grid matrix comprises: (1) foot placement markings employed by the user to establish a reference alignment position; (2) a rear alignment block located proximate said rear border; and (3) a central axis reference line and a plurality of mirror image reference bands that extend from proximate said front border to proximate said rear border; (b) positioning a mirror in front of said mat so that the user, when standing on said mat, sees a reflection of both their image and said mat in said mirror; (c) analyzing the user's postural alignment by comparing the user's mirror image with said grid matrix mirror image; and (d) correcting the user's postural alignment by employing desired exercises and again comparing the user's mirror image to the grid matrix mirror image.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A stationary and dynamic system for utilization in a process of evaluating and correcting a user's posture, wherein the system comprises:
   (a) a mat comprising a substantially planar surface that displays an analysis and exercise region that is delineated by a front border, a rear border, and two opposing side borders;
   (b) a grid matrix formed onto said substantially planar surface within said analysis and exercise region, wherein said grid matrix comprises:
      (i) a single pair of foot-shaped placement markings respectively and equally spaced on left and right portions of a plus-shaped marking being centrally located along and discrete from a single, dashed central axis reference line, the single pair of foot-shaped placement markings employed by the user to establish a reference alignment position;
      (ii) a rear alignment block located proximate to said rear border; and
      (iii) a plurality of mirror image reference bands respectively oriented as mirror images relative to the single, dashed central axis reference line, the plurality of mirror image reference bands and the single, dashed central axis reference line extending from proximate to said front border to proximate to said rear border; and
   (c) a mirror utilized in combination with said mat for body postural analysis and corrective exercise while the user stands and walks on said mat.

2. The mat according to claim 1, further comprising a series of measurement hash marks on each of outer most mirror image reference bands proximate to said rear border.

3. The mat according to claim 1, wherein said mat comprises a sheet of material that may be rolled or folded into a compact form for transport.

4. A stationary and dynamic body postural analysis and corrective exercise system for utilization in a process of evaluating and correcting a user's posture, wherein the system comprises:
   (a) a mat having a substantially planar surface that displays an analysis and exercise region that is delineated by a front border, a rear border, and two opposing side borders;

(b) a grid matrix formed onto said substantially planar surface within said analysis and exercise region, wherein said grid matrix comprises:
  (i) a single pair of foot-shaped placement markings respectively and equally spaced on left and right portions of a plus-shaped marking being centrally located along and discrete from a single, dashed central axis reference line, the single pair of foot-shaped placement markings employed by the user to establish a reference alignment position;
  (ii) a rear alignment block located proximate to said rear border; and
  (iii) a plurality of mirror image reference bands respectively oriented as mirror images relative to the single, dashed central axis reference line, the plurality of mirror image reference bands and the single, dashed central axis reference line extending from proximate to said front border to proximate to said rear border;
(c) a mirror placed to reflect to the user both the user's image and the grid matrix, thereby allowing an analysis of the user's posture for use in conjunction with posture correcting exercises; and
(d) a list of procedures for analyzing and correcting the user's body posture while the user stands and walks on said mat and said mirror in combination.

5. The system according to claim 4, wherein said mat comprises a sheet of material that may be rolled or folded into a compact form for transport.

6. A stationary and dynamic method for analyzing and correcting a user's postural alignment, comprising the steps of:
  (a) placing a postural analysis and corrective exercise mat on a supporting surface, wherein said postural analysis and corrective exercise mat comprises:
    (i) a substantially planar surface that displays an analysis and exercise region that is delineated by a front border, a rear border, and two opposing side borders;
    (ii) a grid matrix formed onto said substantially planar surface within said analysis and exercise region, wherein said grid matrix comprises:
      (1) a single pair of foot-shaped placement markings respectively and equally spaced on left and right portions of a plus-shaped marking being centrally located along and discrete from a single, dashed central axis reference line, the single pair of foot-shaped placement markings employed by the user to establish a reference alignment position;
      (2) a rear alignment block located proximate to said rear border; and
      (3) a plurality of mirror image reference bands respectively oriented as mirror images relative to the single, dashed central axis reference line, the plurality of mirror image reference bands and the single, dashed central axis reference line extending from proximate to said front border to proximate to said rear border;
  (b) positioning a mirror in front of said postural analysis and corrective exercise mat so that the user, when standing and walking on said postural analysis and corrective exercise mat, sees a reflection of both their image and said grid matrix of said postural analysis and corrective exercise mat in said mirror;
  (c) analyzing the user's postural alignment by comparing the user's mirror image while standing and walking with said grid matrix mirror image;
  (d) providing a list of procedures for analysis and correction of the user's body postural alignment; and
  (e) correcting the user's postural alignment by employing said list of procedures for analysis and correction of the user's body postural alignment and comparing the user's mirror image to the grid matrix mirror image.

* * * * *